US009867696B2

United States Patent
Matheny (10) Patent No.: US 9,867,696 B2
(45) Date of Patent: *Jan. 16, 2018

(54) SYSTEMS, APPARATUS AND METHODS FOR SEALING PERIVALVULAR LEAKS

(71) Applicant: CorMatrix Cardiovascular, Inc., Roswell, GA (US)

(72) Inventor: Robert G Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/652,767

(22) Filed: Jul. 18, 2017

(65) Prior Publication Data
US 2017/0312074 A1    Nov. 2, 2017

Related U.S. Application Data

(63) Continuation of application No. 14/483,557, filed on Sep. 11, 2014, now Pat. No. 9,737,399.

(60) Provisional application No. 61/876,540, filed on Sep. 11, 2013.

(51) Int. Cl.
A61F 2/24     (2006.01)
A61F 2/92     (2013.01)

(52) U.S. Cl.
CPC .......... *A61F 2/2412* (2013.01); *A61F 2/2463* (2013.01); *A61F 2250/0069* (2013.01)

(58) Field of Classification Search
CPC ................ A61F 2/2418; A61F 2/2412; A61F 2250/0069; A61F 2/2436; A61F 2230/0054; A61F 2/2409; A61F 2220/0016; A61F 2250/006; A61F 2/2427; A61F 2/246; A61F 2/243; A61F 2/2439; A61F 2/24; A61F 2/2487
See application file for complete search history.

(56) References Cited

U.S. PATENT DOCUMENTS 9,737,399 B2 *   8/2017   Matheny ............... A61F 2/2412

* cited by examiner

*Primary Examiner* — Ann Schillinger
(74) *Attorney, Agent, or Firm* — Francis Law Group (57) ABSTRACT

An expandable support member comprising an ECM composition that is configured to engage an interior region of a prosthetic valve and capable of transitioning from a pre-deployment configuration, where the support member is capable of being positioned at an interior valve region of the valve when the valve is disposed at a cardiovascular valve structure, to a post-deployment configuration when the support member absorbs a first bodily fluid and expands, where an outer surface region of the valve is placed in intimate contact with host cardiovascular tissue of the cardiovascular structure at a first position and seals perivalvular leaks present at the first cardiovascular structure position.

4 Claims, 2 Drawing Sheets

SYSTEMS, APPARATUS AND METHODS FOR SEALING PERIVALVULAR LEAKS

CROSS-REFERENCE TO RELATED APPLICATIONS

This application is a continuation of U.S. application Ser. No. 14/483,557, filed on Sep. 11, 2014, which claims priority to U.S. Provisional Application No. 61/876,540, filed on Sep. 11, 2013.

FIELD OF THE INVENTION

The present invention generally relates to replacement prosthetic valves. More particularly, the present invention relates to an apparatus and method for sealing perivalvular leaks; particularly, during or after a cardiovascular valve replacement.

BACKGROUND OF THE INVENTION

As is well known in the art, the human heart has four valves that control blood flow circulating through the human body. On the left side of the heart is the mitral valve, located between the left atrium and the left ventricle, and the aortic valve, located between the left ventricle and the aorta. Both of these valves direct oxygenated blood from the lungs into the aorta for distribution through the body.

The tricuspid valve, located between the right atrium and the right ventricle, and the pulmonary valve, located between the right ventricle and the pulmonary artery, however, are situated on the right side of the heart and direct deoxygenated blood from the body to the lungs.

The peripheral venous system also includes a number of valves that prevent retrograde blood flow. By preventing retrograde blood flow, the valves found throughout the venous system assist the flow of blood through the veins and returning to the heart.

Normally, the mitral valve has two leaflets and the tricuspid valve has at least two, preferably, three leaflets. The aortic and pulmonary valves, however, have normally at least two, preferably three leaflets, also often referred to as "cusps" because of their half-moon like appearance.

Venous valves are usually of the bicuspid type, with each cusp or leaflet forming a reservoir for blood, which, under pressure, forces the free edges of the cusps together to permit mostly antegrade blood flow to the heart. As discussed in detail below, since a majority of venous blood flow is against gravity while a person is standing, incompetent or destroyed venous valves can cause significant medical problems in the legs, ankles, and feet.

Valve diseases are typically classified into two major categories; stenosis and insufficiency. In the case of a stenosis, the native valve does not open properly, whereby insufficiency represents the opposite effect showing deficient closing properties.

Insufficiency of the inlet (atrioventricular) tricuspid valve to the right ventricle of the heart results in regurgitation of blood back into the right atrium, which, serving to receive blood flow returning in the veins from the entire body, then results, in turn, in suffusion and swelling (edema) of all the organs, most notably in the abdomen and extremities, insufficient forward conduction of blood flow from the right ventricle into the lungs causing compromise of pulmonary function, and ultimately pump failure of the right heart. Collectively these conditions are termed right heart failure, a condition that leads to incapacity and possibly to death if progressive and uncorrected.

Insufficiency of vein function due to the incompetence or destruction of peripheral venous valves leads to acute then chronic swelling of the veins and their dependent lymphatics and tissues. This condition can affect the deep veins of the body, commonly the lower extremities or pelvis, or the superficial veins of the lower extremities in particular, leading to progressive expansion of the veins and further valvular incompetence, a condition known as varicose veins.

Medical conditions like high blood pressure, inflammatory and infectious processes often lead to stenosis and insufficiency. Treatment of heart valve dysfunctions typically include reparation of the diseased heart valve with preservation of the patient's own valve or replacement of the valve with a mechanical or bioprosthetic valve (i.e. "tissue" valve), i.e. a prosthetic valve. Particularly for aortic heart valves, however, it is frequently necessary to introduce a heart valve replacement.

Various prosthetic heart valves have thus been developed for replacement of natural diseased or defective valves. Illustrative are the bioprosthetic "tissue" valves disclosed in Applicant's Co-Pending application Ser. No. 13/560,573.

The implantation of a prosthetic valve, including mechanical valves and bioprosthetic valves, requires a great deal of skill and concentration given the delicate nature of the native cardiovascular tissue and the spatial constraints of the surgical field. It is also critical to achieve a secure and reliable attachment of the valve to host cardiovascular tissue.

Various structures and means have thus been developed to provide a secure and reliable attachment of a prosthetic valve to host cardiovascular tissue. Most surgical techniques comprise suturing the ends of the valve to the annulus of the cardiovascular vessel.

There are numerous drawbacks and disadvantages associated with suturing a valve to host tissue. A major disadvantage is the high risk of a perivalvular leak.

In application Ser. No. 13/560,573 the tissue valve includes a sewing ring that can be employed to suture the ends of the valve to the annulus of the cardiovascular vessel. Although the use of a sewing ring to secure the valve to a cardiovascular vessel can be, and most times is, highly effective, success of the technique is still highly dependent on the skill of the surgeon.

Figure 1:
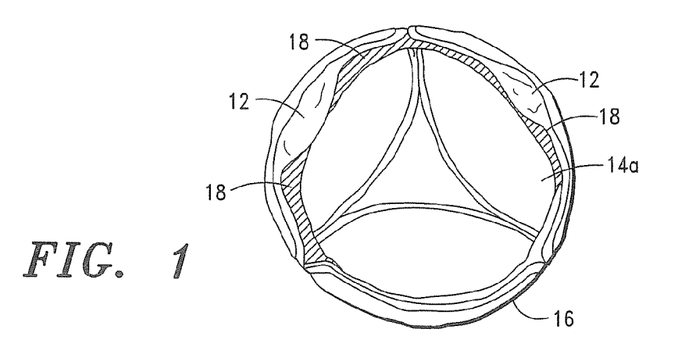
FIG. 1 is a schematic illustration of a replacement valve disposed in a cardiovascular vessel, showing gaps and, hence, perivalvular leak regions therebetween.

Perivalvular leaks are also often encountered during or after a cardiovascular valve replacement due to placement of the replacement valve over native valve leaflets, which are often calcified. As illustrated in FIG. 1, the calcified leaflets 12 are, thus, wedged between the replacement valve 14a and the vessel 16, which results in gaps 18 between the valve 14a and vessel 16 that lead to perivalvular leaks.

There is thus a need to provide an apparatus and method for sealing perivalvular leaks; particularly, leaks encountered during or after a cardiovascular valve replacement.

It is therefore an object of the present invention to provide an apparatus and method for sealing perivalvular leaks; particularly, leaks encountered during or after a cardiovascular valve replacement.

It is another object of the present invention to provide an apparatus for sealing perivalvular leaks that induces regeneration of cardiovascular tissue.

SUMMARY OF THE INVENTION

The present invention is directed to systems, apparatus and methods for sealing perivalvular leaks; particularly, leaks encountered during or after a cardiovascular valve replacement.

In a preferred embodiment, the perivalvular leak sealing apparatus comprises a biocompatible, expandable member that is configured to engage an interior region of a prosthetic valve.

In some embodiments of the invention, the perivalvular leak sealing apparatus comprises a biocompatible shape memory alloy member that is capable of transitioning from a pre-deployment configuration at a first temperature, wherein the expandable member is capable of being positioned proximate the internal valve region when the valve is disposed in a cardiovascular structure, the cardiovascular structure comprising host cardiovascular tissue having a first tissue temperature, to a post-deployment configuration when the expandable member is disposed proximate the cardiovascular tissue and subjected to the first tissue temperature, wherein, when the expandable member is disposed in the internal valve region, the valve outer surface proximate the interior valve region is placed in intimate contact with the host cardiovascular tissue of the cardiovascular structure at a cardiovascular structure target region and seals perivalvular leaks present at the structure target region.

In some embodiments of the invention, the perivalvular leak sealing apparatus comprises a bioremodelable member that is capable of transitioning from a pre-deployment configuration, wherein the expandable member is similarly capable of being positioned at the internal valve region of the valve when the valve is disposed in a cardiovascular structure, to a post-deployment configuration, wherein, when the expandable member is disposed at the internal valve region, the valve outer surface proximate the interior valve region is placed in intimate contact with host cardiovascular tissue of the cardiovascular structure at a cardiovascular structure target region and seals perivalvular leaks present at the structure target region.

In some embodiments of the invention, the bioremodelable material comprises an extracellular matrix (ECM) material. According to the invention, the ECM material can be derived from various mammalian tissue sources including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, omentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

In some embodiments of the invention, the ECM material (and/or ECM expandable member formed therefrom) comprises at least one supplemental biologically active agent (or composition).

In some embodiments of the invention, the biologically active agent comprises a hemostatic agent or composition.

In some embodiments, the hemostatic agent comprises thrombin.

In some embodiments, the hemostatic agent comprises fibrinogen.

In some embodiments, the hemostatic agent is selected from the group comprising fibronectin, plasminogen, aprotinin, α-2-antiplasmin, α-2 macroglobulin, α-1-antitrypsin, epsilon-aminocaproic acid, tranexamic acid, and a plasmin activator inhibitor, e.g., PAI-1 and PAI-2.

In some embodiments of the invention, the biologically active agent comprises a statin, i.e. a HMG-CoA reductase inhibitor, selected from the group comprising atorvastatin, cerivastatin, fluvastatin, lovastatin, mevastatin, pitavastatin, pravastatin, rosuvastatin, and simvastatin.

In some embodiments of the invention, the biologically active agent comprises a cell selected from the group comprising human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some embodiments of the invention, the biologically active agent comprises a growth factor selected from the group comprising a platelet derived growth factor (PDGF), epidermal growth factor (EGF), transforming growth factor-α (TGF-α), transforming growth factor beta (TGF-β), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platelet derived growth factor (PDGF), tumor necrosis factor α (TNA-α), and placental growth factor (PLGF).

In some embodiments, the biologically active agent comprises a pharmacological agent (or composition), i.e. an agent or composition that is capable of producing a desired biological effect in vivo, e.g., stimulation or suppression of apoptosis, stimulation or suppression of an immune response, etc.

According to the invention, the pharmacological agent or composition can comprise, without limitation, antibiotics or antifungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In a preferred embodiment of the invention, the expandable ECM member comprises a flexible, porous, e.g., sponge-like, structure.

In some embodiments of the invention, the expandable member includes or comprises a support (or anchoring) member that is similarly capable of transitioning from a pre-deployment configuration, the support member and/or expandable member similarly being capable of being positioned at the internal valve region of the valve when the valve is disposed in a cardiovascular structure, to a post-deployment configuration, wherein, when the support member and/or expandable member is disposed at the internal valve region, the outer surface of the valve proximate the valve region is placed in intimate contact with host cardiovascular tissue of the cardiovascular structure at a cardiovascular structure target region and seals perivalvular leaks present at the structure target region.

In some embodiments of the invention, the support member comprises a reinforcing ring or band that is positioned in or on the expandable member.

In some embodiments, the support member comprises a microneedle support member having a plurality of biodegradable microneedles or barbs that are configured and positioned to maintain the position of the expandable member and, hence, a valve outer surface proximate host cardiovascular tissue.

In some embodiments, the support member comprises a biodegradable material, including, without limitation, magnesium and an ECM material.

In some embodiments, the support member comprises a biocompatible polymeric material, including, without limitation, Artelon™.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, dermal extracellular matrix, subcutaneous extracellular matrix, gastrointestinal extracellular matrix, i.e. large and small intestines, tissue surrounding growing bone, placental extracellular matrix, omentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from epithelium of mesodermal origin, i.e. mesothelial tissue.

The ECM material can additionally be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

The terms "sponge" and "sponge-like configuration" are used interchangeably herein, and mean and include an elastic, porous structure that is capable of absorbing a bodily fluid when in contact therewith and expanding, i.e. increasing in mass, thereafter.

The terms "biologically active agent" and "biologically active composition" are used interchangeably herein, and mean and include agent that induces or modulates a physiological or biological process, or cellular activity, e.g., induces proliferation, and/or growth and/or regeneration of tissue.

The terms "biologically active agent" and "biologically active composition", as used herein, thus mean and include a hemostatic agent or composition, including, without limitation, thrombin, fibrinogen, fibronectin, plasminogen, aprotinin, α-2-antiplasmin, α-2 macroglobulin, α-1-antitrypsin, epsilon-aminocaproic acid, tranexamic acid, and a plasmin activator inhibitor, e.g., PAI-1 and PAI-2.

The terms "biologically active agent" and "biologically active composition" also mean and include, without limitation, the following growth factors: platelet derived growth factor (PDGF), epidermal growth factor (EGF), transforming growth factor α (TGF-α), transforming growth factor beta (TGF-β), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platelet derived growth factor (PDGF), tumor necrosis factor-α (TNA-α), and placental growth factor (PLGF).

The terms "biologically active agent" and "biologically active composition" also mean and include, without limitation, human embryonic stem cells, fetal cardiomyocytes, myofibroblasts, mesenchymal stein cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, osteopontins, and angiotensin converting enzymes (ACE).

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term's "pharmacological agent", "active agent", "drug" and "active agent formulation" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oxytetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent", "drug" and "active agent formulation" further mean and include the following Class I-Class V antiarrhythmic agents:

(Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antiobiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "pharmacological agent", "active agent", "drug" and "active agent formulation" can further include one or more classes of cytotoxic anti-neoplastic agents or chemotherapy agents, including, without limitation, alkylating agents, cisplatin, carboplatin, oxaliplatin, mechlorethamine, cyclophosphamide, chlorambucil, and ifosfamide. Chemotherapy agents can also include, without limitation, antimetabolites, such as purine analogues, pyrimidine analogues and antifolates, plant alkaloids, such as vincristine, vinblastine, vinorelbine, vindesine, podophyllotoxin, etoposide and teniposide, taxanes, such as paclitaxel and docetaxel, topoisomerase inhibitors, such as irinotecan, topotecan, amsacrine, etoposide, etoposide phosphate and teniposide, cytotoxic antibiotics, such as actinomyocin, bleomycin, plicamycin, mytomycin and anthracyclines, such as doxorubicin, daunorubicin, valrubicin, idarubicin, epirubicin, and antibody treatments, such as abciximab, adamlimumab, alamtuzumab, basiliximab, belimumab, bevacizumab, brentuximab vedotin, canakinumab, cetuximab, certolizumab pego, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumumab, ranibizumab, rituximab, tocilizumab (atlizumab), tositumomab and trastuzumab.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, a amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "therapeutically effective", as used herein, means that the amount of the "pharmacological agent" and/or "biologically active agent" and/or "pharmacological composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "abate", "prevent" and "preventing" are used interchangeably herein, and mean and include reducing the frequency or severity of a condition or disorder. The term does not require an absolute preclusion of the condition or disorder.

The terms "treat" and "treatment" are used interchangeably herein, and mean and include medical management of a patient with the intent to cure, ameliorate, stabilize, or prevent a disease, pathological condition or disorder. The terms include "active treatment", i.e. treatment directed specifically toward the improvement of a disease, pathological condition or disorder, and "causal treatment", i.e. treatment directed toward removal of the cause of the associated disease, pathological condition or disorder.

The terms "treat" and "treatment" further include "palliative treatment", i.e. treatment designed for the relief of symptoms rather than the curing of the disease, pathological condition or disorder, "preventative treatment", i.e. treatment directed to minimizing or partially or completely inhibiting the development of the associated disease, pathological condition or disorder, and "supportive treatment", i.e. treatment employed to supplement another specific therapy directed toward the improvement of the associated disease, pathological condition or disorder.

The terms "prosthetic valve" and "valve" are used interchangeably herein, and mean and include a valve construct that is configured to replace a native cardiovascular valve, such as the valve constructs disclosed in U.S. Pat. Nos. 8,696,744 and 7,998,196, and Co-pending U.S. application. Ser. No. 13/782,024, now U.S. Pat. No. 9,044,319, Ser. No. 13/782,289, now U.S. Pat. No. 8,709,076, Ser. Nos. 13/804,683 and 13/480,347, now U.S. Pat. No. 8,845,719.

The terms "delivery" and "administration" are used interchangeably herein, and mean and include placing a perivalvular leak sealing apparatus or system of the invention in an internal region of a cardiovascular valve through any method appropriate to deliver the perivalvular leak sealing apparatus.

The term "supplemental" and variations of the term, such as "augmented", as used in connection with a "biologically active agent or composition", means and includes the introduction of an additional non-native agent to the bioremodelable or ECM material (and/or an expandable ECM member formed therefrom), and introducing additional native agents to the bioremodelable or ECM material (and/or an expandable ECM member formed therefrom), e.g., fibroblast growth factor-2 (FGF-2) to increase the population of a native agent.

The term "comprise" and variations of the term, such as "comprising" and "comprises," means "including, but not limited to" and is not intended to exclude, for example, other additives, components, integers or steps.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to systems, apparatus and methods for sealing perivalvular leaks; particularly, leaks encountered during or after a cardiovascular valve replacement.

In a preferred embodiment, the perivalvular leak sealing apparatus comprises a biocompatible, expandable member that is configured to engage an interior region of a prosthetic valve.

In some embodiments of the invention, the perivalvular leak sealing apparatus comprises a biocompatible shape memory alloy member that is capable of transitioning from a pre-deployment configuration at a first temperature, wherein the expandable member is capable of being positioned proximate the internal valve region when the valve is disposed in a cardiovascular structure, the cardiovascular structure comprising host cardiovascular tissue having a first tissue temperature, to a post-deployment configuration when the expandable member is disposed proximate the cardiovascular tissue and subjected to the first tissue temperature, wherein, when the expandable member is disposed in the interior valve region, the valve outer surface proximate the interior valve region is placed in intimate contact with the host cardiovascular tissue of the cardiovascular structure at a cardiovascular structure target region and seals perivalvular leaks present at the structure target region.

In some embodiments of the invention, the perivalvular leak sealing apparatus comprises a bioremodelable member that is similarly capable of transitioning from a pre-deployment configuration, wherein the expandable member is capable of being positioned at the interior valve region when the valve is disposed in a cardiovascular structure, to a post-deployment configuration, wherein, when the expandable member is disposed at the internal valve region, the valve outer surface proximate the interior valve region is placed in intimate contact with host cardiovascular tissue of the cardiovascular structure at a cardiovascular structure target region and seals perivalvular leaks present at the structure target region.

In some embodiments of the invention, the bioremodelable material (and, hence, expandable member formed therefrom) comprises an extracellular matrix (ECM) material (hereinafter "expandable ECM member"). According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety. Suitable mammalian tissue sources include, without limitation, small intestine submucosa (SIS), urinary bladder submucosa (UBS), stomach submucosa (SS), central nervous system tissue, dermal extracellular matrix, subcutaneous extracellular matrix, gastrointestinal extracellular matrix, i.e. large and small intestines, tissue surrounding growing bone, placental extracellular matrix, omentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)," "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from epithelium of mesodermal origin, i.e. mesothelial tissue, as well as the basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

As is well known in the art, the noted ECM materials (and, hence, expandable ECM members formed therefrom) are capable of inducing bioremodeling and, hence, regeneration of cardiovascular tissue.

According to the invention, the ECM material can be formed into a particulate, as described in U.S. Pat. Nos. 5,275,826, 6,579,538 and 6,933,326, and Co-Pending application Ser. No. 13/573,569, now U.S. Pat. No. 9,072,816; which are incorporated by reference herein in their entirety, to form a sponge-like expandable ECM member of the invention.

In some embodiments of the invention, the ECM material comprises an acellular, sterilized ECM material. According to the invention, the ECM material can be sterilized and decellularized by various conventional means. In a preferred embodiment of the invention, the ECM material is sterilized and decellularized via a sterilization and decellularization process disclosed in Co-Pending U.S. PCT Application No. PCT/US12/039413 and Co-Pending U.S. application Ser. No. 13/480,140, now U.S. Pat. No. 8,877,224; which are incorporated by reference herein in their entirety.

In some embodiments of the invention, the ECM material (and/or an expandable ECM member formed therefrom) comprises at least one supplemental biologically active agents (or compositions), i.e. an agent or composition that induces or modulates a physiological or biological process, or cellular activity, e.g., hemostatic activity, cell proliferation, and/or growth and/or regeneration of tissue.

In some embodiments of the invention, the biologically active agent comprises a hemostatic agent or composition.

In some embodiments, the hemostatic agent comprises thrombin.

In some embodiments, the hemostatic agent comprises fibrinogen.

In some embodiments, the hemostatic agent is selected from the group comprising fibronectin, plasminogen, aprotinin, $\alpha$-2-antiplasmin, $\alpha$-2 macroglobulin, $\alpha$-1-antitrypsin, epsilon-aminocaproic acid, tranexamic acid, and a plasmin activator inhibitor, e.g., PAI-1 and PAI-2.

In some embodiments of the invention, the biologically active agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

In some embodiments of the invention, the biologically active agent comprises a cell selected from the group comprising human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

In some embodiments of the invention, the biologically active agent comprises a growth factor selected from the group comprising a platelet derived growth factor (PDGF), epidermal growth factor (EGF), transforming growth factor-$\alpha$ (TGF-$\alpha$), transforming growth factor beta (TGF-$\beta$), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platelet derived growth factor (PDGF), tumor necrosis factor $\alpha$ (TNA-$\alpha$), and placental growth factor (PLGF).

In some embodiments of the invention, the biologically active agent comprises includes chitin or a derivative thereof, e.g. chitosan. As set forth in detail in Co-Pending application Ser. No. 13/573,569, now U.S. Pat. No. 9,072,816, chitosan exhibits numerous beneficial properties that provide several beneficial biochemical actions or activities, including anticoagulant activity. See, e.g., Aranaz, et al., *Functional Characterization of Chitin and Chitosan*, Current Chemical Biology, vol. 3, pp. 203-230 (2009).

In some embodiments, the biologically active agent comprises a pharmacological agent (or composition), i.e. an agent or composition that is capable of producing a desired biological effect in vivo, e.g., stimulation or suppression of apoptosis, stimulation or suppression of an immune response, etc.

According to the invention, the pharmacological agent or composition can comprise, without limitation, antibiotics or antifungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the perivalvular leak sealing apparatus comprises a expandable member comprising a biodegradable polymeric material that is similarly capable of transitioning from a pre-deployment configuration, wherein the expandable member is capable of being positioned at an interior valve region of a valve when the valve is disposed in a cardiovascular structure, to a post-deployment configuration, wherein, when the expandable member is disposed at the internal valve region, the valve outer surface proximate the interior valve region is placed in intimate contact with host cardiovascular tissue of the cardiovascular structure at a cardiovascular structure target region and seals perivalvular leaks present at the structure target region.

According to the invention, suitable biodegradable polymeric materials comprise, without limitation, polyhydroxyalkonates (PHAs), polylactides (PLLA) and polyglycolides (PLGA) and their copolymers, for example poly($\epsilon$-caprolactone-co-glycolide), polyanhydrides, and like polymers.

As also indicated above, in some embodiments of the invention, the expandable member includes or comprises a support (or anchoring) member that is similarly capable of transitioning from a pre-deployment configuration, wherein the support member and/or expandable member is capable of being positioned at an internal valve region of a valve when the valve is disposed in a cardiovascular structure, to a post-deployment configuration, wherein, when the support member and/or expandable member is disposed at the internal valve region, the valve outer surface proximate the interior valve region is placed in intimate contact with host cardiovascular tissue of the cardiovascular structure at a cardiovascular structure target region and seals perivalvular leaks present at the structure target region. Suitable support members are disclosed in Co-Pending U.S. application Ser. No. 13/573,226, now U.S. Pat. No. 8,808,363, Ser. No. 13/782,024, now U.S. Pat. No. 9,044,319 and Ser. No. 13/804,683, which are incorporated by reference herein.

In some embodiments of the invention, the support member comprises a reinforcing ring or band that is positioned on or in the expandable member.

In a preferred embodiment of the invention, the support member comprises a biocompatible material.

Thus, in some embodiments, the support member comprises Nitinol®.

In some embodiments, the support member comprises stainless steel.

In some embodiments, the support member comprises a cobalt-chrome nickel alloy.

In some embodiments of the invention, the support member comprises a biocompatible and biodegradable material.

In some embodiments, the support member thus comprises magnesium or an alloy thereof.

In some embodiments of the invention, the metal support members include a coating of an immunomodulating compound that suppresses acute immune responses, while up regulating chronic immune response (i.e. tissue reconstruction).

In some embodiments, the immunomodulating compound comprises a polysaccharide, including, without limitation, GAGs, dextrans, alginate and chitosan.

In some embodiments, immunomodulating compound comprises a polymeric material, including, without limitation, high molecular weight hyaluronic acid (HMW-HA).

In some embodiments, the support member comprises a biocompatible polymeric material selected from the group comprising, without limitation, polyhydroxyalkonates (PHAs), polylactides (PLLA) and polyglycolides (PLGA) and their copolymers, for example poly(ϵ-caprolactone-co-glycolide), polyanhydrides, and like polymers.

In some embodiments, the support member comprises Artelon™.

In some embodiments, the support member comprises a cross-linked ECM material.

In some embodiments, the support member comprises a microneedle support member, such as disclosed in Co-Pending U.S. application Ser. No. 13/686,131, now U.S. Pat. No. 8,778,012, having a plurality of biodegradable microneedles or barbs that are configured and positioned to maintain the desired position of the valve outer surface or region proximate host tissue at a target cardiovascular structure region and any perivalvular leaks present at the cardiovascular structure target region.

In some embodiments, the microneedles comprise drug-eluting members that facilitate the direct administration of a biologically active agent to host tissue, e.g. cardiovascular tissue.

According to the invention, the perivalvular leak sealing apparatus of the invention can be delivered to an internal region of a replacement or prosthetic valve via various conventional means. In a preferred embodiment, the perivalvular leak sealing apparatus of the invention are delivered to an internal region of a prosthetic valve via percutaneous delivery, i.e. feeding a guide wire through a cardiovascular vessel.

Referring now to FIGS. 2-5, a first embodiment of a perivalvular leak sealing apparatus of the invention (denoted "20") will be described in detail.

Referring first to FIG. 1, as stated above, typically, a replacement valve 14a, such as the prosthetic valves disclosed in Co-Pending U.S. application. Ser. No. 13/782,024, now U.S. Pat. No. 9,044,319, and Ser. No. 13/804,683, is disposed over native valve leaflets 12, which are often calcified. The calcified leaflets 12 are thus wedged between the replacement valve 14a and the vessel 16, resulting in gaps 18 between the valve 14a and vessel 16, which can, and often will, lead to one or more perivalvular leaks.

According to the invention, the perivalvular leak sealing apparatus illustrated in FIGS. 2-3 and 6-7, as well as other embodiments thereof, can be readily positioned in a valve proximate the gaps 18 to seal any perivalvular leaks present at the gaps 18.

Figure 2:
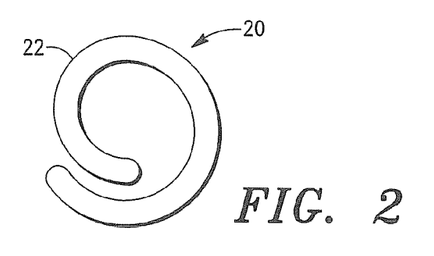
FIG. 2 is a side plan view of one embodiment of a perivalvular leak sealing apparatus in a pre-deployment configuration, in accordance with the invention.
Figure 3:
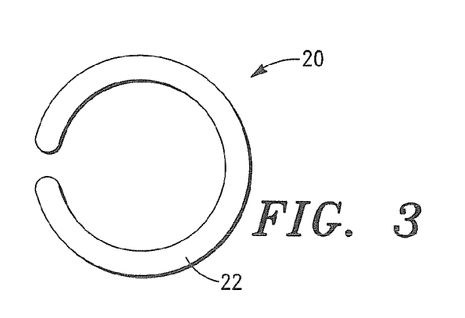
FIG. 3 is a side plan view of the perivalvular leak sealing apparatus shown in FIG. 2 in a post-deployment configuration, in accordance with the invention.
Figure 4:
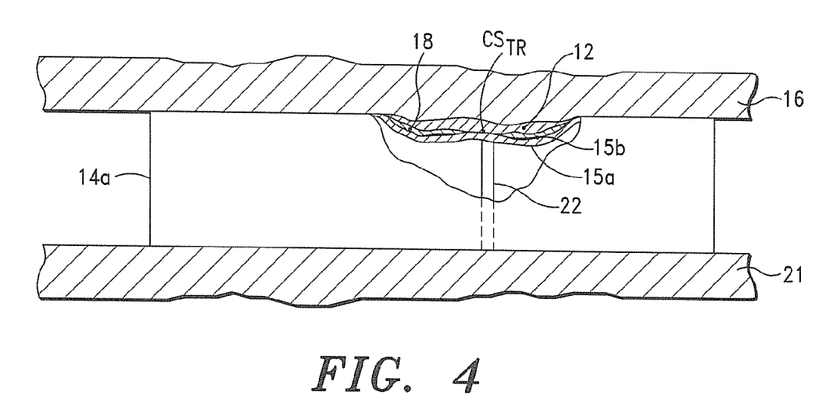
FIG. 4 is a side plan view of the perivalvular leak sealing apparatus shown in FIG. 3 positioned at an internal valve region of a valve disposed in a cardiovascular vessel, in accordance with the invention.
Figure 5:
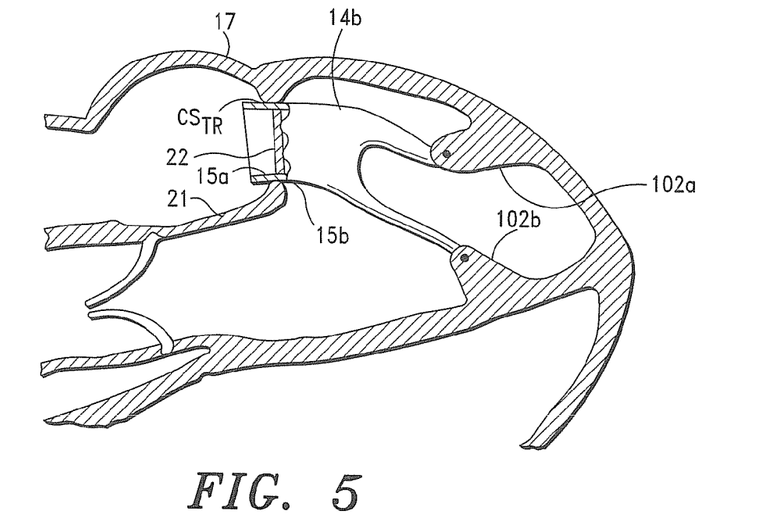
FIG. 5 is a side plan view of the perivalvular leak sealing apparatus shown in FIG. 3 positioned at an internal valve region of a valve disposed in a cardiovascular structure, in accordance with the invention.

As indicated above, in some embodiments of the invention, the sealing apparatus 20 comprises a biocompatible, expandable member 22 that is capable of transitioning from a pre-deployment configuration (as shown in FIG. 2), wherein the expandable member 22 is capable of being positioned at an interior valve region 15a of the valve 14a (and valve 14b) when the valve 14a (and valve 14b) is disposed in a cardiovascular vessel 16 (as shown in FIG. 4) or structure 17 (as shown in FIG. 5), to a post-deployment configuration (as shown in FIG. 3), wherein, when the expandable member 22 is disposed at the interior valve region 15a, the valve outer surface or region 15b proximate the interior valve region 15a is placed in intimate contact with host cardiovascular tissue 21 of the cardiovascular vessel 16 or structure 17 at a cardiovascular structure target region (denoted "$CS_{TR}$") and seals perivalvular leaks present at the structure target region "$CS_{TR}$".

As indicated above, the expandable member can comprise various biocompatible materials, including any of the aforementioned biodegradable polymeric materials.

According to the invention, the expandable member 22 can also comprise various pre-deployment configurations or shapes, e.g. oblong, circular, etc. In a preferred embodiment, the expandable member 22 has a substantially circular post-deployment configuration.

In some embodiments of the invention, the expandable member 22 comprises a bioremodelable material, more preferably, an extracellular matrix (ECM) material (hereinafter "expandable ECM member") derived from a mammalian tissue source, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, omentum extracellular matrix, cardiac extracellular matrix, e.g., pericardium and/or myocardium, kidney extracellular matrix, pancreas extracellular matrix, lung extracellular matrix, and combinations thereof.

In some embodiments of the invention, the expandable ECM member 22 has a sponge-like structure, i.e. a flexible, porous structure that is capable of absorbing a bodily fluid and expanding when disposed thereto.

In some embodiments, the ECM material (and/or expandable ECM member 22 formed therefrom) comprises at least one supplemental biologically active agent (or composition).

In some embodiments of the invention, the biologically active agent comprises a hemostatic agent or composition.

In some embodiments, the hemostatic agent comprises thrombin.

In some embodiments, the hemostatic agent comprises fibrinogen.

In some embodiments, the hemostatic agent is selected from the group comprising fibronectin, plasminogen, aprotinin, α-2-antiplasmin, α-2 macroglobulin, α-1-antitrypsin, epsilon-aminocaproic acid, tranexamic acid, and a plasmin activator inhibitor, e.g., PAI-1 and PAI-2.

In some embodiments of the invention, the biologically active agent comprises a statin, i.e. a HMG-CoA reductase inhibitor, selected from the group comprising atorvastatin, cerivastatin, fluvastatin, lovastatin, mevastatin, pitavastatin, pravastatin, rosuvastatin, and simvastatin.

In some embodiments of the invention, the biologically active agent comprises chitosan.

In some embodiments of the invention, the biologically active agent comprises one or more of the aforementioned cells, including, without limitation, human embryonic stem cells, mesenchymal stem cells, parenchymal cells, epithelial cells and endothelial cells.

In some embodiments of the invention, the biologically active agent comprises one or more of the aforementioned growth factors, including, without limitation, a platelet derived growth factor (PDGF), transforming growth factor-α (TGF-α), transforming growth factor beta (TGF-β), fibroblast growth factor-2 (FGF-2), basic fibroblast growth factor (bFGF) and vascular epithelial growth factor (VEGF).

In some embodiments of the invention, the biologically active agent comprises one or more of the aforementioned pharmacological agents or compositions, including, without limitation, an antibiotic, anti-viral agent, and anti-inflammatory.

As indicated above, in some embodiments of the invention, the perivalvular leak sealing apparatus 22, i.e. expandable member, comprises a biocompatible shape memory alloy member that is configured to engage the interior valve region 15a of a valve (for purposes of illustration only "valve 14a"), the expandable member 22 similarly being capable of transitioning from a pre-deployment configuration at a first temperature, wherein the expandable member 22 is capable of being positioned within the valve 14a at an interior valve region 15a when the valve 14a is disposed is disposed in a cardiovascular vessel 16 or structure, the cardiovascular vessel 16 and structure comprising host cardiovascular tissue 21 having a first tissue temperature, to a post-deployment configuration when the expandable member 22 is disposed proximate the cardiovascular tissue 21 and subjected to the first tissue temperature, wherein, when the expandable member 22 is disposed in the internal valve region 15a, the valve outer surface or region 15b proximate the interior valve region 15a is placed in intimate contact with the host cardiovascular tissue 21 of the cardiovascular vessel 16 or structure at a cardiovascular structure target region "$SC_{TR}$" and seals perivalvular leaks present at the structure target region $SC_{TR}$.

Figure 6:
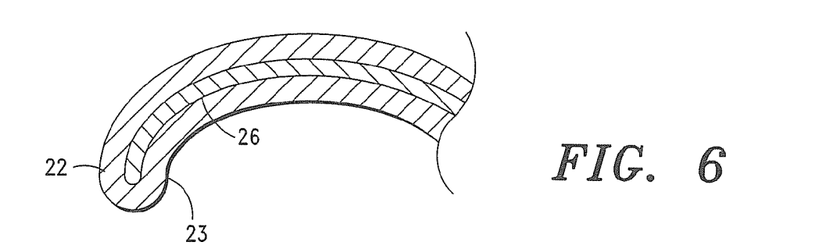
FIG. 6 is a partial side plan sectional view of one embodiment of a perivalvular leak sealing apparatus having a support member disposed within the expandable member, in accordance with the invention.
Figure 7:
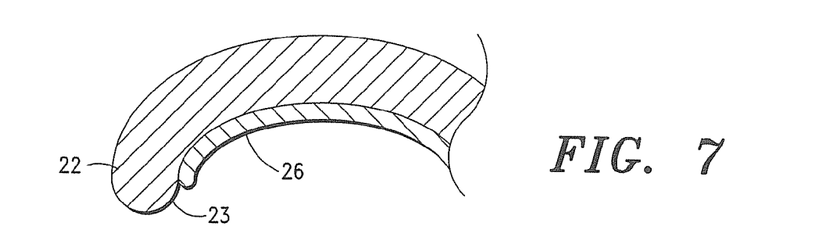
FIG. 7 is a partial side plan sectional view of another embodiment of a perivalvular leak sealing apparatus having a support member disposed proximate the outer surface of the expandable member, in accordance with the invention.

Referring now to FIGS. 6-7, there are shown further embodiments of the expandable member 22, wherein the expandable member 22 includes a support (or anchoring) member 26. As illustrated in FIGS. 6-7, in a preferred embodiment, the support member 26 comprises a reinforcing ring or band.

In some embodiments, the support member 26 is disposed in the expandable member, as shown in FIG. 6. In some embodiments, the support member 26 is disposed proximate the outer surface 23 of the expandable member 22, as shown in FIG. 7.

According to the invention, the support member is similarly capable of transitioning from a pre-deployment configuration, wherein the support member 26 (and, hence, expandable member 22 associated therewith) is capable of being positioned in the interior valve region 15a of a cardiovascular valve (for purposes of illustration only "valve 14a"), to a post-deployment configuration, wherein, when the support member 26 (and, hence, expandable member 22 associated therewith) are disposed in the interior valve region 15a, the valve outer surface or region 15b proximate the interior valve region 15a is placed in intimate contact with the host cardiovascular tissue 21 of a cardiovascular vessel 16 or structure at a cardiovascular structure target region "$SC_{TR}$" and seals perivalvular leaks present at the structure target region $SC_{TR}$.

According to the invention, the support member 26 can comprise any of the aforementioned biocompatible metals, including, Nitinol®, magnesium, stainless steel, and cobalt-chrome nickel alloys.

The support member 26 can also comprise a polymeric material, such as Artelon™, or a cross-linked ECM material.

In some embodiments of the invention, the support member 26 comprises Nitinol®. As discussed in detail in U.S. Pat. No. 8,808,363, the Nitinol® support members are capable of transitioning from a pre-deployment configuration at a first temperature, to a post-deployment configuration at a second temperature, which, in some embodiments, comprises host tissue temperature.

Figure 8:
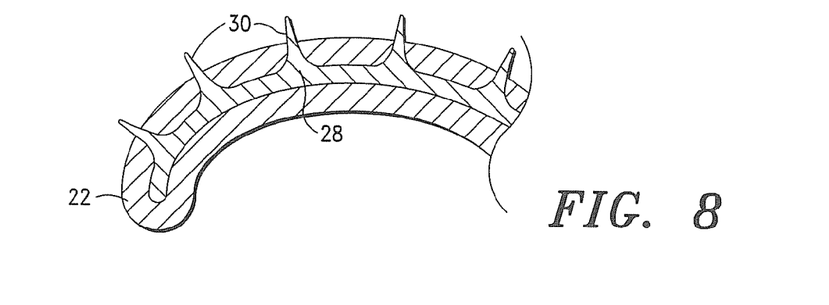
FIG. 8 is a partial side plan sectional view of another embodiment of a perivalvular leak sealing apparatus having a microneedle support member, in accordance with the invention.

Referring now to FIG. 8, in some embodiments, the support member comprises a microneedle support member 28 having a plurality of biodegradable microneedles (or barbs) 30. In a preferred embodiment, the microneedles 30 are configured and positioned to maintain the position of the expandable member 22 proximate host tissue of a cardiovascular structure.

In some embodiments, the microneedles 30 comprise drug-eluting members that facilitate the direct administration of a biologically active agent to host tissue, e.g. cardiovascular tissue 21.

According to the invention, when the perivalvular leak sealing apparatus 20 comprises one of the aforementioned ECM materials and includes the support member 26 shown in FIGS. 6-7 and/or the microneedle support member 28, shown in FIG. 8, and is positioned in the interior valve region 15a of a cardiovascular valve 14a or 14b and transitions to (or is in) a post-deployment configuration, the valve outer surface or region 15b proximate the interior valve region 15a is placed in intimate contact with the host cardiovascular tissue 21 of a cardiovascular vessel 16 or structure 17 at a cardiovascular structure target region "$SC_{TR}$" and abates, i.e. substantially reduces or eliminates, perivalvular leaks present at the structure target region $SC_{TR}$. Thereafter, cardiovascular tissue is regenerated via the bioremodelable ECM material to further seal the perivalvular leak(s), i.e. a two-stage sealing process.

As will readily be appreciated by one having ordinary skill in the art, the present invention provides numerous advantages. Among the advantages are the following:

The provision of a perivalvular leak sealing apparatus that can be readily employed to effectively seal perivalvular leaks.

The provision of a two-stage perivalvular leak sealing apparatus that can be readily employed to effectively seal perivalvular leaks.

The provision of perivalvular leak sealing apparatus that induce cell proliferation, bioremodeling and regeneration of new cardiovascular tissue and tissue structures with site-specific structural and functional properties.

The provision of perivalvular leak sealing apparatus that can administer a biologically active agent to cardiovascular tissue and, thereby, produce a desired biological and/or therapeutic effect.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A perivalvular leak sealing apparatus, comprising:

a bioremodelable two-stage leak abatement structure consisting of a prosthetic cardiovascular tissue valve configured to be positioned proximate a cardiovascular valve structure, said prosthetic cardiovascular tissue valve comprising an interior valve region and an outer surface region, and a remodelable, expandable member configured to engage said interior valve region of said prosthetic cardiovascular tissue valve, said prosthetic cardiovascular tissue valve further comprising first acellular extracellular matrix (ECM) from a first mammalian tissue source, said first acellular ECM defining a biological leak sealing component, said expandable member further comprising a flexible, porous structure configured to expand upon exposure to and absorption of a bodily fluid, said expandable member consisting of second acellular ECM from a second mammalian tissue source, said expandable member defining a physiomechanical leak abatement component, said physiomechanical leak abatement component being configured to transition from a pre-deployment configuration, wherein said physiomechanical leak abatement component is capable of being positioned at said interior valve region when said prosthetic cardiovascular tissue valve is disposed at a first cardiovascular valve structure, to a post-deployment configuration when said physiomechanical leak abatement component absorbs a first bodily fluid and expands, wherein, when said physiomechanical leak abatement component is disposed in said interior valve region of said prosthetic cardiovascular tissue valve, said outer surface region of said prosthetic cardiovascular tissue valve proximate said interior valve region is placed in intimate contact with host cardiovascular tissue of said first cardiovascular valve structure at a cardiovascular structure target position and abates at least one perivalvular leak present at said cardiovascular structure target position during a first perivalvular leak sealing stage, and wherein, after a first period of time after said outer surface region of said prosthetic cardiovascular tissue valve is placed in said intimate contact with said host cardiovascular tissue of said first cardiovascular valve structure at said cardiovascular structure target position, said prosthetic cardiovascular tissue valve remodels and said biological leak sealing component induces remodeling of said host cardiovascular tissue and regeneration of new cardiovascular tissue at said cardiovascular structure target position, wherein said prosthetic cardiovascular tissue valve further abates said perivalvular leak during a second sealing stage.

2. The perivalvular leak sealing apparatus of claim 1, wherein said first mammalian tissue source comprises a tissue source selected from the group consisting of the small intestine submucosa, urinary bladder submucosa, stomach submucosa and mesothelial tissue.

3. The perivalvular leak sealing apparatus of claim 1, wherein said second mammalian tissue source comprises a tissue source selected from the group consisting of the small intestine submucosa, urinary bladder submucosa, stomach submucosa and mesothelial tissue.

4. The perivalvular leak sealing apparatus of claim 1, wherein said second acellular ECM comprises a supplemental growth factor selected from the group consisting of a basic fibroblast growth factor (bFGF), transforming growth factor beta (TGF-$\beta$), and vascular epithelial growth factor (VEGF).

* * * * *